United States Patent [19]

Vanderbilt et al.

[11] Patent Number: 4,950,735

[45] Date of Patent: Aug. 21, 1990

[54] BIODEGRADABLE POLYAMIDES

[75] Inventors: David P. Vanderbilt; Donald R. Cowsar, both of Birmingham, Ala.; Richard L. Dunn, Fort Collins, Colo.; James P. English, Birmingham, Ala.

[73] Assignee: Sharpoint L.P., Reading, Pa.

[21] Appl. No.: 224,316

[22] Filed: Jul. 26, 1988

[51] Int. Cl.$^5$ .................. C08G 63/08; C08G 69/26
[52] U.S. Cl. .................................. 528/354; 528/335
[58] Field of Search .............. 424/78; 528/335, 354, 528/358

[56] References Cited

U.S. PATENT DOCUMENTS 4,064,086 12/1977 Cowsar et al. ..................... 528/354

FOREIGN PATENT DOCUMENTS 0030822 3/1980 Fed. Rep. of Germany .

OTHER PUBLICATIONS

Tanquary, et al., Thermoplastic Crosslinked Polyamides of 3,3-bis(hydroxymethyl)glutaric acid, J. Polym. Sci., Polym. Lett. Ed., 15(5): 471–474, '77.

Dunn et al. Sythesis & Prop. of a New Thermoplastic Hydrogel, Trans. of 8th Annual Meeting Society for Biomaterials, 4/24–27, 1982, Biom. Soc., '82.

Terry, et al., Comparison of the Mechanical Properties of P-HEMA and P-HPMA Hydrogels with a New Synthetic Polyamide Hydrogel, In: Craig, R. C., ed.: Transactions of the 9th Annual Meeting of the Society for Biomaterials; Apr. 27–May 1, 1983; Birmingham, Ala. Biomaterials Society; 50.

*Primary Examiner*—Joseph L. Schofer
*Assistant Examiner*—Carmen B. Pili-Curtis
*Attorney, Agent, or Firm*—William H. Elliot, Jr.

[57] ABSTRACT

Biodegradable polyamides, useful as absorable sutures and as controlled release binder materials, are prepared by condensing 4,4'-spirobibutyrolactone with a primary diamine, optionally in the presence of a nylon salt, leading to homopolymers containing lactam structural units, or to random copolymers.

11 Claims, No Drawings

BIODEGRADABLE POLYAMIDES

This invention is in the field of organic polymer chemistry. More specifically, this invention relates to novel polyamides having both pendant hydroxyl functionality and lactam groups in the polymer backbone. These polymers are compatible with living tissue and are biodegradable, making them especially useful as absorbable suture materials and controlled release carrier, encapsulating, or excipient materials for bio-active agents, for example.

In one aspect, homopolymers of this invention are prepared by opening the lactone rings of difunctional 4,4'-spirobibutyrolactone (SBBL) with a diamine. In another aspect of this invention, a copolymer is produced when the aforesaid polymerization is carried out in the presence of a dibasic acid and additional diamine.

Homopolymers similar to those of this invention were disclosed in U.S. Pat. No. 4,064,086, which describes both a linear polyamide containing hydroxyl groups, and adducts thereof crosslinked with diisocyanates via the pendant hydroxyl groups. The homopolymers of the instant invention are distinguished from the polyamides of U.S. Pat. No. 4,064,086 in terms of the method by which they are prepared and their chemical structure. The homopolymers of the instant invention include lactam groups. Although the polymers disclosed in U.S. Pat. No. 4,064,086 were characterized as thermoplastic hydrogels, biodegradation was not disclosed.

Sutures may be classified as absorbable or nonabsorbable, and absorbable sutures may be monofilaments or multifilaments. The absorbable sutures are typically either synthetic materials, such as poly(glycolide), poly(lactide-co-glycolide), or natural materials such as silk and catgut. Due to their high modulus of elasticity, the synthetic sutures are stiffer than natural catgut or silk; therefore they are employed as braided multifilament yarns to reduce the stiffness. Braiding is detrimental because the added surface roughness may actually abrade through weak tissues. Braided sutures may also inhibit knot run-down due to surface roughness of the braid, and coatings are routinely applied to serve as lubricants.

There are wide variations in tissue types, degrees of trauma, and rates of healing. Although several attempts have been made, no one has developed an ideal suture material; consequently, a need exists for suture materials in a variety of strengths, sizes, and rates of degradation. There are, however, several desirable characteristics that all absorbable sutures should possess. The material should have good handling characteristics. It should hold tissue for proper healing with minimal tearing and tissue damage; it should have good tensile and knot strength; it should be capable of being easily tied into stable surgical knots; it should be dimensionally stable in the body; it should be sterilizable; and it should be absorbable by living tissue without causing adverse reactions. While numerous materials have been and continue to be investigated for use as absorbable sutures, none has completely satisfied all these criteria.

It is known that nylons 6- and 6,6 eventually degrade in vivo, but their rates of biodegradation are too slow for most practical uses. Certain polyamides, such as alpha-benzoylated nylon 6,3 and the alternating copolymers of glycine (nylon 2)/nylon 6 and serine/nylon 6, are considerably more susceptible to biodegradation than either nylon 6 or nylon 6,6.

Materials that have been proposed to resolve the stiffness problem include the copolyoxalates, copolymers of p-dioxanone and other poly(ether esters), and poly(ester amides). In the poly(ether ester) series, flexibility is imparted by the presence of the ether linkages; the same linkages increase the hydrophilicity of the polymer, enhancing the overall rate of hydrolysis or biodegradation. Chain flexibility in straight-chain aliphatic polyesters can be increased by increasing the length of the aliphatic chain. However, increasing the aliphatic chain length causes a simultaneous decrease in hydrophilicity and in the rate of hydrolysis.

Thus, an objective of the instant invention is to produce a series of polyamides which overcomes the several problems of the prior art absorbable suture materials. This objective is attained in novel organic polymers, the structural formula of which includes a backbone containing n biradical units of the formula

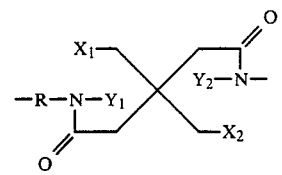

joined randomly with m biradical units of the formula

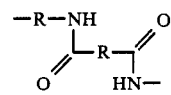

wherein
n is a positive integer;
m is either zero or a positive integer; each R independently is a hydrocarbon radical;
$X_1$ is —OH and $Y_1$ is —H, or $X_1$ and $Y_1$ together constitute a chemical bond in a lactam ring;
$X_2$ is —OH and $Y_2$ is —H, or $X_2$ and $Y_2$ together constitute a chemical bond in a lactam ring;
said backbone being capped with a radical selected from

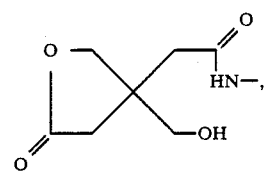

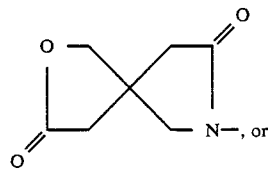

—NH$_2$, and also

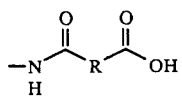

when m is a positive integer;

with the proviso that the polymer contains lactam units when m is zero.

It will be recognized that polymers within the aforesaid description may exist as isomers, including stereoisomers, and it should be understood this invention contemplates and includes all such isomers.

In the event that m is zero, the aforesaid description includes a series of homopolymers which are prepared by condensing 4,4'-spirobibutyrolactone with various primary diamines. The resulting homopolymers of this invention include lactam units within their structural formulae. These lactam units may be viewed formally as produced by elimination of water between $X_1$ and $Y_1$, or $X_2$ and $Y_2$. Among the possible homopolymers obtainable by varying the nature of the diamine, it is preferred that the hydrocarbon radical R be aliphatic or alicyclic and that it contain 4–14 carbon atoms. Among the aliphatic diamines, pentamethylenediamine and hexamethylenediamine are especially useful, and hexamethylenediamine is preferred. Examples of useful alicyclic diamines are 1,4-cyclohexanebis(methylamine) and 4,4'-methylenebis(cyclohexylamine). Other useful diamines are disclosed in U.S. Pat. No. 4,064,086, incorporated herein by reference.

When both n and m are positive integers, the aforesaid description includes copolymers of 4,4'-spirobibutyrolactone and a first diamine combined with a nylon derived from a dibasic acid and a second diamine. Although the first and second diamines need not be the same, it is preferred that they are the same in order to simplify the polymer structure and minimize the number of reactants. Preferred diamines include aliphatic and alicyclic diamines having 4–14 carbon atoms, especially those named above in connection with the homopolymers. Pentamethylenediamine and hexamethylenediamine are especially useful. Although wide variations are possible in the dibasic acid, it is preferred that the dibasic acid component of the nylon be aliphatic and contain 3–9 carbon atoms. Glutaric and especially adipic acid are preferred. Although the copolymers of this invention may contain lactam units in their structural formulae, that feature is not a requisite element.

The properties of a copolymer containing a given nylon are dependent upon the lactone/nylon ratio. This ratio may vary from about 90/10 to about 10/90, but the ratio is preferably in the range 25/75 to 75/25. A 50/50 ratio provides a polymer especially useful for sutures when one of the polymer units is nylon 6,6 and hexamethylenediamine is also present in the lactone portion.

In the description which follows, the polymers of this invention are sometimes referred to using a condensed nomenclature scheme similar to that employed for nylons, in which the term "6,6", for example, refers to the polymer of hexamethylenediamine (the first "6") and adipic acid (the second "6"). Accordingly, "6,S5" refers to the homopolymer of hexamethylenediamine, sometimes also referred to as "HMDA", and 4,4'-spirobibutyrolactone, while "6,S5:6,6 (50:50)" refers to the 50:50 (mol:mol) copolymer of hexamethylenediamine, 4,4'-spirobibutyrolactone:hexamethylenediamine, adipic acid.

The polymers within the scope of this invention are prepared by various techniques. The homopolymers can be prepared by reacting 4,4'-spirobibutyrolactone (SBBL) directly with the desired diamine. Alternatively, it may be advantageous to prepare the polymer from a preformed salt of 3,3-bis(hydroxymethyl)glutaric acid (BHMGA) and the diamine. Copolymers within the scope of this invention are conveniently prepared by reacting a nylon salt containing the desired dibasic acid and diamine with either the lactone/diamine mixture or the appropriate glutarate/diamine salt. These syntheses are illustrated below.

The inherent viscosities (IV's) of SBBL-containing polyamides were determined in trifluoroethanol at a concentration of 0.5 g/dL at 30° C. Infrared spectra were obtained from thin films on NaCl plates.

An estimate of the lactone and lactam groups in the homopolymers was obtained from IR spectra by comparing the ratios of the lactone carbonyl stretch to the amide II absorptions and the amide I to amide II absorptions, respectively. These ratios were calculated from the peak areas of the respective absorptions in the IR spectra. A polymer consisting of acyclic secondary amide groups alone should show no contribution by lactone carbonyl (abt. 1775 cm$^{-1}$), and the lactone carbonyl/amide II ratio should be zero. Similarly, this polymer should have an amide I/amide II ratio of about 1.1, which is the case for nylon 6,6. Because the lactam structure gives rise to an amide I band, but no amide II band, amide I/amide II ratios greater than about 1.1 should be indicative of polymers containing lactam groups. Therefore, the larger the amide I/amide II ratio, the greater the amount of lactam present in the polymer. Similarly, the larger the lactone carbonyl/amide II ratio, the greater the amount of lactone present.

Model compounds can be employed to quantify the lactone, lactam and secondary amide structures present in the polymer. Three model compounds (gamma-butyrolactone, N-methylpyrrolidone, and N-methylacetamide) were chosen as materials representative of carbonyl groups present in the polymers. Furthermore, these compounds were all liquids at room temperature, which permitted IR spectra under the same conditions as the polymers (i.e., in an amorphous phase). Binary solutions of gamma-butyrolactone/N-methylacetamide and N-methylpyrrolidone/N-methylacetamide of known mol % were prepared, and an IR spectrum (linear absorbance mode) of each solution was obtained. From each IR spectrum, the areas under the lactone, amide I, and amide II absorptions were determined. Areas were determined by weighing three photocopy cutouts of each absorption and determining an average weight. Two calibration curves were then plotted: log(amide I/amide II) vs mol % N-methylpyrrolidone and lactone carbonyl/amide II vs mol % gamma-butyrolactone. From these two plots, the percentage of each carbonyl species in a homopolymer could be calculated. The results obtained using the IR analysis described above were compared in a few cases with results obtained by more costly and time-consuming NMR analyses; based on that comparison, the conclusions reached using IR analysis and reported below should be viewed as semiquantitative.

The polymer molecular weights set forth in the Tables which follow were determined by IR end group analysis, assuming one lactone end group per polymer chain, unless it is indicated the molecular weights were determined by vapor phase osmometry (VPO).

EXAMPLE I

Salt of 3,3-Bis(Hydroxymethyl)glutaric Acid and Hexamethylenediamine

SBBL was synthesized in four steps from dibromopentaerythritol in a manner similar to that described in U.S. Pat. No. 4,064,086.

SBBL (20.0 g, 0.128 mol) was treated with two equivalents of aqueous NaOH (1.0 M) at room temperature, and in a separate flask, hexamethylenediamine (HMDA, 14.87 g, 0.128 mol) was combined with an equivalent amount of 2.0 N $H_2SO_4$. The solutions were combined, and the majority of the water was removed with a rotary evaporator. Anhydrous ethanol (500 ml) was added to the flask, and the precipitate ($Na_2SO_4$) was removed by filtration. The filtrate was reduced in volume to an oil, and fresh ethanol was added. The remainder of the water was removed via azeotropic distillation with ethanol until a white solid formed in the flask. The solid was washed thoroughly with ethanol, filtered and dried in vacuo overnight at room temperature, affording 35.2 g (89%) of the polysalt of 3,3-bis(hydroxymethyl)glutaric acid (BHMGA) and HMDA, mp 132°–133° C. (dec).

EXAMPLE II

Homopolymer of SBBL and HMDA (6,S5)

A. From SBBL/HMDA

To a glass-lined pressure vessel was added 25.35 g (0.162 mol) of SBBL and 20.0 g (0.172 mol) of HMDA. The vessel was sealed, deoxygenated by pressurization-depressurization with $N_2$, and finally pressurized to 100 psig with $N_2$. The vessel was immersed in an oil bath at 240° C. for 3 hrs and then allowed to cool to room temperature. The glass liner containing the product was placed inside a glass tube of larger diameter, and a vacuum (abt. 1 mm Hg) was applied to the apparatus. The assemblage was heated gradually to 230° C. under vacuum, and it was maintained at that temperature for 3 hrs. The molten mass was then cooled slowly to 120° C., where it was maintained for 1.5 hr. and then allowed to cool slowly to room temperature. The resultant straw-colored product had an IV of 1.00 dL/g.

B. From BHMGA/HMDA Salt.

In a glass liner was placed 5.99 g (0.0194 mol) of 3,3-bis(hydroxymethyl)glutaric acid/HMDA salt and 0.14 g (0.0012 mol) of HMDA. The liner was sealed inside a stainless steel pressure vessel and deoxygenated and pressurized with $N_2$ (100 psig) as described in Example IIA. The vessel was placed in an oil bath and maintained at 240° C. for 4 hr and then was allowed to cool to room temperature. The resultant prepolymer was dried overnight at room temperature under vacuum. The prepolymer was then heated under vacuum (about 1 mm Hg) to 230° C., maintained at that temperature for 3 hr, and then slowly cooled to 130° C. over 2 hr, and then held at 130° C. for 1.5 hr. The polymer was then allowed to cool to room temperature under vacuum. The IV of the product was 1.05 dL/g.

Tables 1–3 illustrate the effect of various reaction conditions on the product obtained from the BHMGA/HMDA salt.

TABLE 1

HOMOPOLYMERIZATION OF BHMGA/HMDA SALT AT CONSTANT TEMPERATURE (170° C.) AND PRESSURE (130 psig $N_2$)

| Sample No. C790 | Initial pressure $N_2$, psig | Reaction time, h | IV, dL/g | Lactone, mol % | Lactam, mol % | 2° Amide, mol % | $\overline{M}_n$ |
|---|---|---|---|---|---|---|---|
| -133-1 | 130[a] | 24 | 0.19 | 2 | 57 | 41 | — |
| -137-1[b] | —[c] | — | 0 36 | 4 | 52 | 44 | 3250 |
| -134-1 | 130[a] | 12 | 0.15 | 5 | 43 | 52 | — |
| -137-2[b] | —[c] | — | 0.25 | 5 | 66 | 29 | 2530 |
| -135-1 | 130[a] | 6 | 0.12 | 3 | 29 | 68 | — |
| -137-3[b] | —[c] | — | 0.16 | 12 | 47 | 41 | 1100 |
| -136-1 | 130[a] | 3 | 0.12 | 4 | 0 | 96 | — |
| -137-4[b] | —[c] | — | 0.14 | 11 | 65 | 24 | 1130 |

[a]Added 0.2 mL $H_2O$/2.0 g salt.
[b]Vacuum step performed on postpressure polymer of preceding entry.
[c]RT to 210° C., 1 h (0.1 mm); 210° C., 1 h (0.1 mm); 210° C., to 100° C., 1 h (0.1 mm).

TABLE 2

HOMOPOLYMERIZATION OF BHMGA/HMDA SALT AT CONSTANT TIME (24 H) AND TEMPERATURE (160° C.)

| Sample No. C790 | pressure $N_2$, psig | Initial pressure $N_2$ + $H_2O$, psig | Final IV, dL/g | Lactone, mol % | Lactam, mol % | 2° Amide, mol % | $\overline{M}_n$ |
|---|---|---|---|---|---|---|---|
| -142-1 | 0[a] | 60 | 0.11 | 6 | 0 | 94 | — |
| -142-2[b] | —[c] | — | 0.18 | 7 | 63 | 30 | 1860 |
| -143-1 | 50[a] | 135 | 0.12 | 6 | 19 | 75 | — |
| -143-2[b] | —[c] | — | 0.20 | 5 | 66 | 29 | 2590 |
| -144-1 | 100[a] | 205 | 0.12 | 7 | 25 | 68 | — |
| -144-2[b] | —[c] | — | 0.19 | 5 | 62 | 33 | 2310 |
| -145-1 | 150[a] | 275 | 0.12 | 7 | 27 | 66 | — |
| -145-2[b] | —[c] | — | 0.18 | 6 | 63 | 31 | 2110 |
| -146-1 | 200[a] | 360 | 0.13 | 7 | 25 | 68 | — |

TABLE 2-continued
HOMOPOLYMERIZATION OF BHMGA/HMDA SALT AT CONSTANT TIME (24 H) AND TEMPERATURE (160° C.)

| Sample No. C790 | pressure N$_2$, psig | Initial pressure N$_2$ + H$_2$O, psig | Final IV, dL/g | Lactone, mol % | Lactam, mol % | 2° Amide, mol % | $\overline{M}_n$ |
|---|---|---|---|---|---|---|---|
| -146-2[b] | —[c] | — | 0.19 | 6 | 58 | 36 | 2100 |

[a]Added 5.0 mL H$_2$O/2.0 g salt.
[b]Vacuum step performed on postpressure polymer of preceding entry.
[c]RT to 170° C. (200 mm); 170° C., 20 h (200 mm).

TABLE 3
HOMOPOLYMERIZATION OF BHMGA/HMDA SALT FOR 24 H

| Sample No. C790 | Initial pressure N$_2$, psig | Temp, °C. | IV, dL/g | Lactone, mol % | Lactam, mol % | 2° Amide, mol % | $\overline{M}_n$ |
|---|---|---|---|---|---|---|---|
| -150-1 | 0[a] | 160 | 0.13 | 7 | 32 | 61 | — |
| -150-2[b] | —[c] | — | 0.17 | 7 | 52 | 41 | 1890 |
| -151-1 | 200[a] | 160 | 0.15 | 6 | 36 | 58 | — |
| -151-2[b] | —[c] | — | 0.18 | 6 | 46 | 48 | 2240 |
| -152-1 | 0[a] | 170 | 0.15 | 5 | 39 | 56 | — |
| -152-2[b] | —[c] | — | 0.19 | 5 | 50 | 45 | 2350 |
| -153-1 | 200[a] | 170 | 0.16 | 7 | 41 | 52 | — |
| -153-2[b] | —[c] | — | 0.20 | 4 | 59 | 37 | 2990 |

[a]No H$_2$O added.
[b]Vacuum step performed on postpressure polymer of preceding entry.
[c]RT to 200° C., 1 h (760 mm); 200° C., 1 h (240 mm); 200° C. to 100° C., 1 h (240 mm to 5 mm)

In general, optimum production of both homopolymers and copolymers having reasonably high molecular weights utilizes a three-step process. In the first step, the reactants are melted (generally about 230°-250° C.) under inert gas pressure (e.g., 100 psig N$_2$ initial pressure) for about 3-4 hours to effect oligomerization. A 1-5 percent excess of diamine may be utilized. In the second step, the prepolymer is heated (usually above 200° C.) under vacuum, e.g., 1-10 mm Hg, to melt it; this is continued until the melt thickens and the evolution of gas slows, typically 2-3 hours. In the third stage, the polymer is allowed to cool and is then held at 100°-140° C. for several (typically 3-4) hours in the solid state. If the polymer is held at this temperature too long, cross-linking may occur. The cross-linking can be reversed, however, by reheating the polymer above its melting temperature and the third stage repeated.

The properties of other homopolymers similarly prepared are shown in Table 4.

TABLE 4
EXAMPLES OF OTHER HOMOPOLYMERS CONTAINING SBBL

| Sample No. | Polymer type and composition[a] | IV, dL/g | $\overline{M}_n$ (VPO) | Method |
|---|---|---|---|---|
| E179-15-1 | 6,S5 | 1.00 | 4,300 | II A. |
| D526-73-1 | 6,S5 | 1.05 | | II B. |
| E179-22-1 | C8,S5[c] | 0.61 | 4,300 | II A. |
| D526-107-2 | 5,S5 | 0.48 | | II A. |
| D526-116-2 | P,S5[b] | 0.08 | | II A. |
| D526-120-2 | C13,S5 | 0.11 | | II A. |

[a]Diamine/diacid. Diamines: 5 = 1,5-pentanediamine; 6 = 1,6-hexanediamine; P = piperazine; C8 = 1,4-cyclohexanebis(methylamine); C13 = 4,4'-methylenebis-(cyclohexylamine).
[b]Outside the scope of this invention.
[c]Other samples of C8,S5 polymers, separately prepared, were cross-linked with hexamethylenediisocyanate and spun into fibers.

EXAMPLE III
Copolymer of BHMGA/HMDA and Nylon; 6S5:6,6 (50:50)

To a glass liner was added 35.2 g (0.114 mol) of BHMGA/HMDA salt, 29.95 g (0.114 mol) of nylon 6,6 salt, and 0.84 g (0.0072 mol) of HMDA. The liner was placed inside a pressure vessel and then deoxygenated and pressurized with N$_2$ as described above. The vessel was heated at 240° C. for 4 hrs and cooled. The mass was heated in vacuo to 230° C., maintained at 230° C. for 3 hrs, cooled slowly to 135° C., and maintained at 135° C. for 16 h. The resultant copolymer would not dissolve in the usual solvents. The mass was reheated to 225° C. in vacuo where it became molten. (1.5 h) and then was recooled to room temperature. The copolymer was soluble at this stage and had an IV of 0.78 dL/g. The remainder of the sample was heated in a vacuum oven at 110° C. for 4 hrs. The IV of the resultant copolymer was 1.75 dL/g.

Substantially the same copolymers can also be prepared by using SBBL and HMDA in place of the BHMGA/HMDA salt. The properties of other copolymers similarly prepared, but incorporating SBBL and other diamines or dibasic acids are shown in Table 5.

TABLE 5
EXAMPLES OF OTHER COPOLYMERS CONTAINING SBBL

| Sample No. | Polymer type and composition[a] | IV, dL/g | $\overline{M}_n$ (VPO) | Method |
|---|---|---|---|---|
| C790-124-2 | 6,S5:6,6 | (25:75) 1.12 | | SALT |
| D526-82-2 | 6,S5:6,6 | (50:50) 1.75 | | SALT |
| D526-83-2 | 6,S5:6,6 | (50:50) 1.78 | | |
| E179-24-1[b] | 6,S5:6,6 | (50:50) 1.80 | 17,400 | |
| D526-39-2 | 6,S5:6,6 | (60:40) 0.77 | | SALT |
| D526-70-1 | 6,S5:6,6 | (75:25) 0.98 | | SALT |
| D526-128-2 | 4,S5:4,6 | (50:50) 0.53 | | |
| D526-110-2 | 5,S5:5,5 | (50:50) 0.47 | | |
| D526-111-2 | 6,S5:6,5 | (50:50) 0.33 | | |

TABLE 5-continued

EXAMPLES OF OTHER COPOLYMERS CONTAINING SBBL

| Sample No. | Polymer type and composition[a] | IV, dL/g | $\overline{M}_n$ (VPO) | Method |
|---|---|---|---|---|
| E179-28-1[b] | C8,S5:C8,6 | (50:50) 1.54 | 7,200 | |
| D526-124-2 | C13,S5:C13,6 | (50:50) 0.34 | | |

[a]Diamine, SBBL: nylon diamine, diacid (mol:mol). Diamines: 4 = 1,4-butanediamine; 5 = 1,5-pentanediamine; 6 = 1,6-hexanediamine (HMDA); C8 = 1,4-cyclohexanebis(methylamine); C13 = 4,4'-methylenebis(cyclohexylamine). Diacids: 5 = glutaric acid; 6 = adipic acid.
[b]Reprecipitated sample.

It will be evident that both the homopolymers and the copolymers of this invention can be cross-linked with difunctional reagents which react with pendant hydroxyl groups, e.g., diisocyanates. Suitable difunctional reagents as well as the manner of their reaction to cross-link polymers of the general nature described herein are set forth in U.S. Pat. No. 4,064,086, incorporated herein by reference.

The utility of polyamides within the scope of this invention was evaluated in fiber-spinning trials, by in vitro hydrolysis studies, by in vivo implantation experiments, and by measuring the controlled release of bioactive agents from drug/polyamide blends. Results of these experiments are presented below.

EXAMPLE IV

Fiber Spinning

A sample of 6,S5:6,6 (50:50) copolymer (IV 0.78) was employed in fiber-spinning trials. Monofilaments were melt spun on a ram extruder (0.6 in. diameter bore) in two spinning trials. The first trial was made with a spinneret having a single orifice 0.020 in. in diameter and 0.040 in. in length to determine the approximate spinneret size and spinning conditions required for preparing monofilament suitable for orienting to a 4-0 suture size. A second trial was then made with a spinneret having a single 0.047 in. diameter orifice about 0.094 in. in length to prepare a sufficient quantity of monofilament with a 4-0 suture size for evaluation. The conditions used in each of these spinning trials are given in Table 6.

The monofilaments were oriented on a draw winder. The conditions used for orienting each sample are given in Table 7.

The diameters of the oriented fibers were measured on a Zeiss polarizing microscope equipped with an eyepiece micrometer disk. The tensile properties were measured on an Instron tester with a gauge length of 5 in. and a crosshead speed of 5 in./min. The chart speed was also 5 in./min. The diameters and tensile properties of the fibers are also given in Table 7.

TABLE 6

MELT-SPINNING CONDITIONS AND DIAMETER OF MONOFILAMENTS

| Melt-spinning conditions | Sample B285 | | | |
|---|---|---|---|---|
| | -81-1 | -81-2 | -85-1 | -85-2 |
| Block temp, °C. | 206 | 206 | 203 | 203 |
| Feed rate, cm$^3$/min | 0.5 | 0.5 | 0.5 | 0.5 |
| Ram pressure, psi | 105 | 150 | 35 | 65 |
| Take-up speed, ft/min | 25.0 | 43.0 | 12.0 | 11.5 |
| Diameter, mils (approx) | 8 | 6 | 14 | 14 |

TABLE 7

ORIENTING CONDITIONS, DIAMETER, AND TENSILE PROPERTIES OF MONOFILAMENTS

| Orienting conditions diameter, and tensile properties | Sample B285 | | | Polypropylene[a] | Nylon 6,6 |
|---|---|---|---|---|---|
| | -81-1-2 | -81-2-3 | -85-1-2 | | |
| Draw ratio | 6.3X | 6.1X | 6.3X | | |
| Plate temp. °C. | 80 | 80 | 80 | | |
| Diameter, mm | 0.0980 | 0.0882 | 0.1764 | 0.2399 | 0.1650 |
| Suture size | 6-0 | 6-0 | 4-0 | 3-0 | 4-0 |
| Denier | 76 | 68 | 224 | 413 | 283 |
| Tenacity, g/d | 1.61 | 1.46 | 1.39 | 5.2 | 4.7 |
| Elongation at break, % | 22 | 23 | 27 | 43.4 | 36.6 |
| Initial modulus, g/d | 10.1 | 19.9 | 19.5 | | |
| Initial modulus, psi $-10^5$ | 4.53 | 9.86 | 7.96 | 3.43 | 4.96 |
| Tensile factor | 7.5 | 7.0 | 7.2 | 34.3 | 28.4 |
| Moisture regain, % | — | — | — | — | 5.4 |

[a]Commercial suture material outside the scope of this invention.

EXAMPLE V

In Vitro Hydrolysis Studies

Accelerated Studies: 90° C. A weighed amount (abt. 0.2 g) of granulated polymer (to pass a #20 mesh sieve) was placed in each of several 10-mL serum vials, and 10-mL of 0.2 M NaH$_2$PO$_4$ (adjusted to pH 7.2) was added. The vials (14 per polymer) were placed in an oven maintained at 90° C., and vials were removed periodically. The polymer residues in the vials were recovered by filtration or isolated by drawing off the buffer solution via pipet, and they were dried in vacuo at room temperature for at least 18 hr. The polymer residues were reweighed, and the percentage of mass recovered for each residue was calculated; the results appear in Table 8.

TABLE 8

IN VITRO HYDROLYSIS (90° C.)
% Mass Recovered

| Time/day | PCL[a] | 6,S5 | 6,S5:6,6 (75:25) | 6,S5:6,6 (60:40) | 6,S5:6,6 (50:50) |
|---|---|---|---|---|---|
| 0 | 100 | 100 | 100 | 100 | 100 |
| 0.125 | 99.8 | 85.4 | 100 | 100 | |
| 0.25 | 99.5 | 84.3 | 100 | 98.9 | |
| 0.5 | 99.9 | 77.3 | 87.8 | 97.0 | 100 |
| 1 | 99.3 | 40.7 | 60.8 | 80.4 | 84.2 |
| 2 | 99.0 | 13.4 | 37.5 | 81.6 | 76.9 |
| 3 | 100 | 0.0 | 35.1 | 63.1 | |
| 4 | 99.9 | | 19.4 | 50.9 | 56.9 |

TABLE 8-continued

IN VITRO HYDROLYSIS (90° C.)
% Mass Recovered

| Time/day | PCL[a] | 6,S5 | 6,S5:6,6 (75:25) | 6,S5:6,6 (60:40) | 6,S5:6,6 (50:50) |
|---|---|---|---|---|---|
| 5 | 99.7 | | 12.2 | | |
| 6 | 98.8 | | 7.8 | 35.3 | 46.5 |
| 8 | 95.3 | | 5.4 | 26.3 | 41.0 |
| 10 | 82.9 | | 7.4 | | |
| 12 | 61.3 | | 6.2 | 22.2 | 38.7 |
| 15 | 44.6 | | | | |
| 16 | | | | 22 0 | |
| 19 | 16.0 | | 7.3 | | 37.1 |
| 20 | | | | 20.3 | |
| 23 | 12.0 | | | | |
| 24 | | | | 21.3 | 38.3 |
| 30 | | | 4.2 | 22.2 | 37.7 |

[a]Polycaprolactone

One-Year Study: 37° C. A second in vitro hydrolysis study was conducted at 37° C. in the manner described above. A somewhat larger particle size (to pass a #8 mesh sieve) was used in this study. The hydrolyses of four experimental polymers (two homopolymers and two 50:50 copolymers), as well as a polycaprolactone control, were studied; the results appear in Table 9.

TABLE 9

IN VITRO HYDROLYSIS (37° C.)
% Mass Remaining

| Time/weeks | PCL[a] | 6,S5 | C8,S5:C8,6 (50:50) | 6,S5:6,6 (50:50) | C8,S5 |
|---|---|---|---|---|---|
| | 100 | 100 | 100 | 100 | 100 |
| 0.43 | 101.7 | 82.6 | 99.8 | 98.3 | 89 |
| 1 | 100.2 | 80.5 | 99.6 | 96.2 | 83.1 |
| 2 | 100.1 | 78.3 | 100 | 95.7 | 79.6 |
| 3 | 99.7 | 75.5 | 98.6 | 94.9 | 78.6 |
| 4 | 99.8 | 76 | 98.3 | 96.8 | 78.7 |
| 6 | 99.8 | 80.7 | 98.5 | 97.8 | 85.3 |
| 9 | 100.1 | 72.7 | 96.5 | 94.4 | 76 |
| 13 | 99.3 | 67.1 | 95.2 | 94.5 | 74.4 |
| 18 | 99 | 62.2 | 94.7 | 94.7 | 76.1 |
| 24 | 99.6 | 58.3 | 95 | 92.7 | 72.2 |
| 30 | 99.2 | 51.8 | 94.9 | — | 71.2 |
| 36 | 99.3 | 44.6 | 96 | 91.1 | 70.6 |
| 44 | 99.1 | 34.3 | 93.2 | 90 | 67.9 |
| 52 | 98.7 | 26.4 | 94.7 | 87.4 | 65.8 |

[a]Polycaprolactone

EXAMPLE VI

In Vivo Implantation

One experimental 6,S5:6,6 (50:50) copolymer, one C8,S5:C8,6 (50:50) copolymer and a nylon 6,6 control were implanted subcutaneously in the backs of male New Zealand white rabbits. One-inch-square film samples (abt. 0.0025 in. thick) of known mass were sterilized with ethylene oxide before use. Three subcutaneous pockets were formed on the back of each anesthetized rabbit, and one sample of each polymer was implanted in each of 15 rabbits. The incisions were closed with stainless steel wound clips. Three animals were sacrificed at 2, 3, 8, 13, and 24 weeks after implantation. At necropsy, the implants were recovered when possible, and the surrounding tissues were excised for histological examination. The retrieved films were cleansed of adhering tissues and dried in vacuo at room temperature. The films were reweighed; the results appear in Table 10.

TABLE 10

IN VIVO IMPLANTATION
% Mass Recovered

| Time, wks | Sample | | |
|---|---|---|---|
| | 6,S5:6,6(50:50) | nylon 6,6 | C8,S5:C8,6(50:50) |
| 0 | 100 | 100 | 100 |
| 2 | 66.8 | ND | 64 |
| 3 | 88.2 | ND | 58 |
| 8 | 26.9 | 96.6 | 29.2 |
| 13 | 9.6 | 99.9 | 7.7 |
| 24 | NR | 96.9 | NR |

NR = no polymer could be recovered
ND = result not determined

The implanted copolymers were found to be highly fragmented after only two weeks in vivo. After 24 weeks in vivo, most of the implants had been absorbed as judged by visual inspection, but the absorption was not total, because small fragments of polymer could be seen under the microscope. The nylon 6,6 control implant did not lose mass or decrease in IV to any significant extent in 24 weeks.

In general, the tissue responses to the implanted copolymers were considered relatively mild and were graded using criteria which included fibrosis, inflammation, vascularity, edema, foreign-body reaction, and abscess formation. The polymers of this invention and nylon 6,6 gave similar mild responses with respect to fibrosis, inflammation, edema, foreign-body reaction, and vascularity.

EXAMPLE VII

Drug/Polyamide Blends

Blends containing 25 wt % progesterone and similar blends containing 1 to 5 wt % insulin were prepared by evaporation of trifluoroethanol solutions containing a 6,S5 homopolymer, a 6,S5:6,6 (50:50) copolymer and a poly(DL-lactide-co-glycolide) copolymer ("DL-PLG"). Progesterone and insulin were selected as the bio-active agents in these tests as representative of therapeutic drugs in general, progesterone being a steroidal hormone of relatively low molecular weight and insulin being a polypeptide of relatively high molecular weight.

The blends were extruded into monolithic rods on a Tinius Olsen extrusion plastometer. The extrusion conditions appear in Table 11.

TABLE 11

| Sample No. C389 | EXTRUSION CONDITIONS | | | |
|---|---|---|---|---|
| | Drug/polymer Blend | Temp, °C. | Extrusion wt, kg | Diam mm |
| -126-5 | progesterone/homopolymer | 70.3 | 7.19 | 2.11 |
| -126-6 | progesterone/50:50 copolymer | 130.9 | 27.49 | 1.23 |
| -126-7 | progesterone/DL-PLG | 72.4 | 20.40 | 1.63 |
| -136-1 | insulin/DL-PLG | 71.4 | 30.72 | 1.31 |
| -136-2 | insulin/homopolymer | 71.4 | 30.72 | 2.31 |
| -136-3 | insulin/50:50 copolymer | 166.0 | 30.72 | 1.23 |

EXAMPLE VIII

Release of Drugs From Blends

The release of progesterone from drug/polymer blends was determined by immersing triplicate samples of each blend in separate containers with 25 mL of an aqueous solution containing 27.5 wt % ethanol. The receiving fluid was changed periodically for fresh ethanol solution, and solution absorbance was measured at 246.5 nm. A standard curve of absorbance versus progesterone concentration was used to quantify the mass released. The results appear in Table 12.

TABLE 12

IN VITRO RELEASE OF PROGESTERONE FROM 25% - LOADED MONOLITHIC RODS

| Polymer | Time, h | Cumulative fraction of progesterone released (Avg. of 3 samples) |
|---|---|---|
| 6,S5 | 0.5 | 0.33 |
| | 1.0 | 0.53 |
| | 2.0 | 0.85 |
| 6,S5;6,6 | 0.5 | 0.20 |
| (50:50) | 1.0 | 0.32 |
| | 2.0 | 0.47 |
| | 3.5 | 0.61 |
| | 7.0 | 0.78 |
| | 24.0 | 0.97 |
| | 48.0 | 0.98 |
| | 72.0 | 0.98 |
| | 240.0 | 0.98 |
| DL-PLG | 0.5 | 0.0084 |
| (75:25) | 1.0 | 0.0086 |
| | 2.0 | 0.0088 |
| | 3.5 | 0.0092 |
| | 7.0 | 0.011 |
| | 24.0 | 0.017 |
| | 48.0 | 0.025 |
| | 240.0 | 0.068 |

Experiments were also undertaken to prepare and test tablets containing insulin and the aforesaid polymers. The tablets were prepared by compression sintering at room temperature under about 100,000 psi. Controlled release was subsequently observed; about 40% of the insulin was released from homopolymer-containing tablets in 48 hours. The release of insulin was examined by immersing triplicate samples of each blend in separate containers with 1 mL of Sorenson's phosphate buffer, pH 7.3. The receiving fluid was exchanged for fresh buffer and analyzed for insulin. The release profile obtained with implants prepared from the homopolymer appears in Table 13.

TABLE 13

IN VITRO RELEASE OF INSULIN FROM 25% - LOADED COMPRESSION SINTERED TABLETS PREPARED WITH 6,S5 HOMOPOLYMER

Cumulation Fraction of Insulin Released

| | C389-147 | | |
|---|---|---|---|
| Time, h | -2a | -2b | -2c |
| 1 | 0.13 | 0.12 | 0.13 |
| 2 | 0.17 | 0.15 | 0.15 |
| 3 | 0.21 | 0.19 | 0.18 |
| 19 | 0.29 | 0.31 | 0.27 |
| 45 | 0.43 | 0.44 | 0.37 |

Surprisingly, when either the homopolymers or the copolymers of this invention are degraded by hydrolysis, the loss of polymer mass occurs approximately linearly with time, especially during the early stages of degradation. While not being bound by this explanation, these zero-order (time independent) degradation kinetics suggest that the polymers degrade either by a surface erosion mechanism or by an "unzippering" mechanism involving chain ends, rather than by random chain scissioning in the bulk of the polymer. Zero-order degradation kinetics clearly distinguishes these polymers from the known poly(glycolides), poly(lactide-coglycolides), polycaprolactone, and similar aliphatic polyesters, as well as the poly(ether-esters) and the poly(ester amides) of the prior art.

When polymers degrade in vitro and in vivo by mechanisms leadings to zero-order mass-loss kinetics, such polymers are especially useful in formulating novel drug delivery systems (implants, microcapsules, etc.) for pharmaceuticals requiring constant, long term delivery rates. Moreover, they have exceptional utility in drug-releasing implants designed to medicate food animals ( pigs, sheep, cattle, chickens, etc.), because implants can be prepared from which no polymer residues remain in tissues after drug release is complete.

What is claimed is:

1. An organic polymer, the structural formula of which includes
a backbone containing n biradical units of the formula

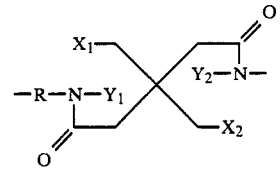

joined randomly with m biradical units of the formula

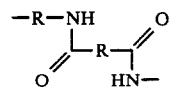

wherein n is a positive integer;

m is either zero or a positive integer; each R independently is a hydrocarbon radical;

$X_1$ is —OH and $Y_1$ is —H, or $X_1$ and $Y_1$ together constitute a chemical bond in a lactam ring;

$X_2$ is —OH and $Y_2$ is —H, or $X_2$ and $Y_2$ together constitute a chemical bond in a lactam ring;

said backbone being capped with a radical selected from

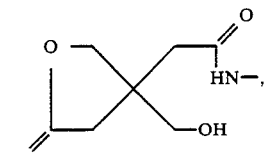

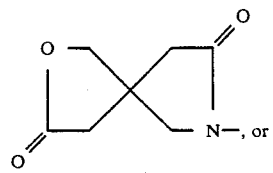

—NH$_2$, and also

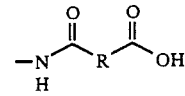

when m is a positive integer;

with the proviso that the polymer backbone contains lactam units when m is zero.

2. A polymer according to claim 1 wherein m is zero and the polymer is a homopolymer.

3. A polymer of claim 2 wherein R is selected from aliphatic and alicyclic groups containing 4–14 carbon atoms.

4. A polymer of claim 3 wherein R is an aliphatic group selected from pentamethylene and hexamethylene.

5. A polymer of claim 3 wherein R is an alicyclic group selected from 1,4-cyclohexanebis(methyl) and 4,4'-methylenebis(cyclohexyl).

6. A polymer of claim 4 wherein R is hexamethylene.

7. A polymer according to claim 1 wherein m is a positive integer and the polymer is a copolymer.

8. A polymer of claim 7 wherein each R is selected from aliphatic and alicyclic groups containing 4–14 carbon atoms.

9. A polymer of claim 8 wherein said aliphatic groups are selected from pentamethylene and hexamethylene and said alicyclic groups are selected from 1,4-cyclohexanebis(methyl) and 4,4'-methylenebis(cyclohexyl).

10. A polymer according to claim 1 which is cross-linked via a difunctional reagent which reacts with hydroxyl groups.

11. A polymer according to claim 10 wherein said reagent is a diisocyanate.

* * * * *